United States Patent [19]

Koll

[11] Patent Number: 4,485,824

[45] Date of Patent: Dec. 4, 1984

[54] METHOD AND APPARATUS FOR COLLECTING AND/OR GROWING PROTECTED BIOLOGICAL SPECIMENS

[75] Inventor: Laurel A. Koll, Ruleville, Miss.

[73] Assignee: E & K Corporation, Ruleville, Miss.

[21] Appl. No.: 353,220

[22] Filed: Mar. 1, 1982

[51] Int. Cl.³ .............................................. A61B 10/00
[52] U.S. Cl. .................................... 128/756; 128/759; 435/295; 435/296; 604/1
[58] Field of Search .................... 128/749, 756–759; 604/1; 435/295, 296, 810

[56] References Cited

U.S. PATENT DOCUMENTS

| | | | |
|---|---|---|---|
| 1,711,352 | 4/1929 | Jeffreys | 604/1 X |
| 3,163,160 | 12/1964 | Cohen | 128/759 |
| 3,394,699 | 7/1968 | Koett | 128/2 |
| 3,491,747 | 1/1970 | Robinson | 128/757 |
| 3,513,830 | 5/1970 | Kalayjian | 128/2 |
| 3,674,007 | 7/1972 | Freis | 128/2 |
| 3,776,220 | 12/1973 | Monaghan | 128/759 |
| 3,796,211 | 3/1974 | Kohl | 128/2 B |
| 3,800,781 | 4/1974 | Zalucki | 128/749 |
| 3,995,618 | 12/1976 | Kingsley et al. | 128/2 B |
| 4,014,746 | 3/1977 | Greenspan | 435/295 X |
| 4,023,559 | 5/1977 | Gaskell | 128/2 W |
| 4,136,680 | 1/1979 | Southworth | 128/213 |
| 4,157,709 | 6/1979 | Schuster et al. | 128/759 |
| 4,184,483 | 1/1980 | Greenspan | 128/759 |
| 4,223,093 | 9/1980 | Newman et al. | 435/295 |
| 4,227,537 | 10/1980 | Snciu et al. | 128/756 |
| 4,235,244 | 11/1980 | Abele et al. | 128/749 |
| 4,312,950 | 1/1982 | Snyder et al. | 128/759 |
| 4,318,414 | 3/1982 | Schuster et al. | 128/759 |
| 4,324,262 | 4/1982 | Hall | 128/756 |

FOREIGN PATENT DOCUMENTS 2031733 12/1979 United Kingdom ............... 128/759

Primary Examiner—Edward M. Coren
Assistant Examiner—John E. Hanley
Attorney, Agent, or Firm—Cushman, Darby and Cushman

[57] ABSTRACT

Method and apparatus for collecting and/or growing anaerobic or aerobic biological specimens. A slidable inner rod and outer tube assembly is provided with rear, middle and front seals which define two coaxial sealed chambers of variable volume within the rod and tube assembly. The front chamber is controllably unsealed to receive a biological specimen. The front chamber is then resealed by manipulation of the tube and rod assembly which may also thereafter cause passage of a biological culture growth medium, transport materials, etc. from a rear chamber into the front chamber by reducing the volume of the rear chamber. The biological specimen is thus collected and may be transferred to a growth medium or the like in a completely protected environment immediately after its collection within an internal organ (for example) of a living body.

35 Claims, 4 Drawing Figures

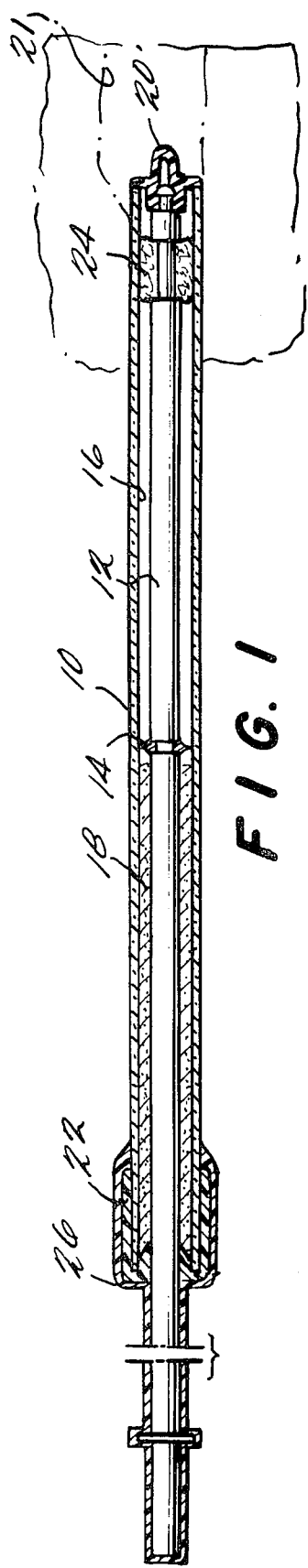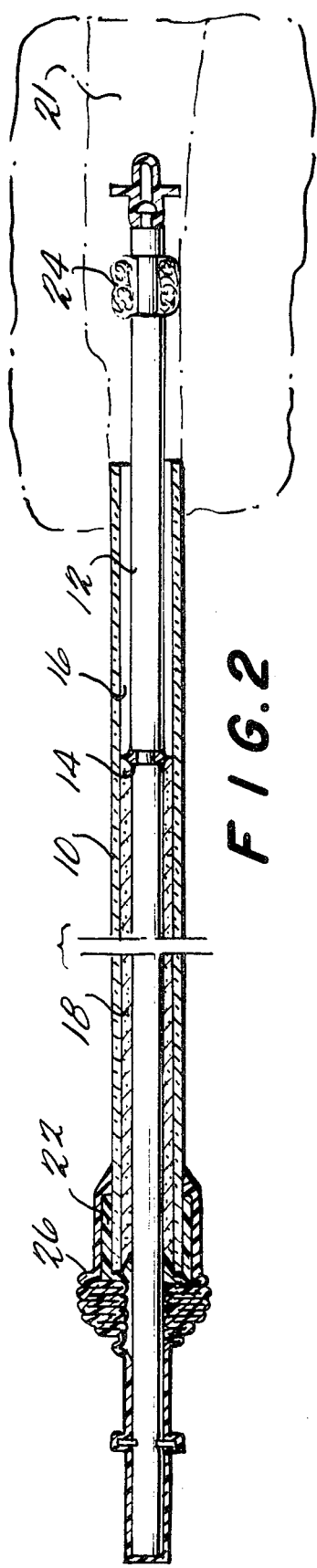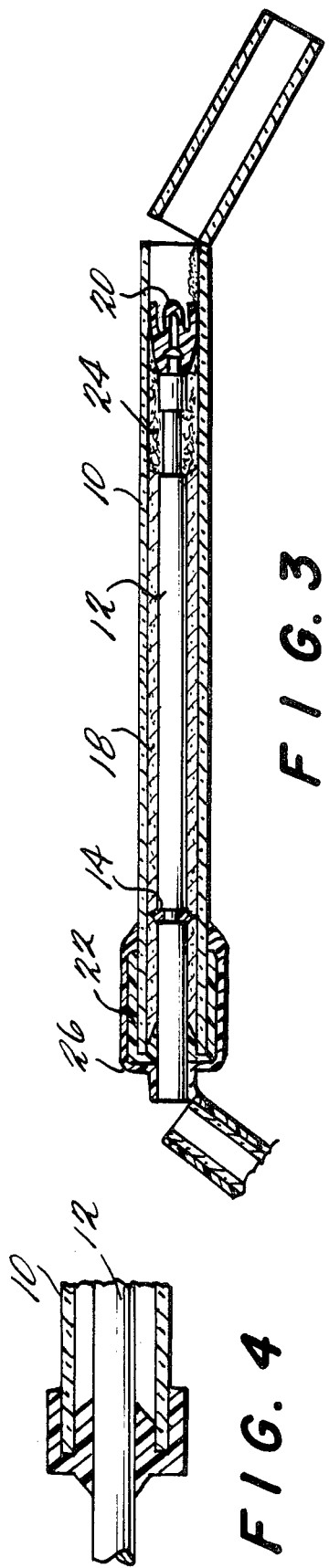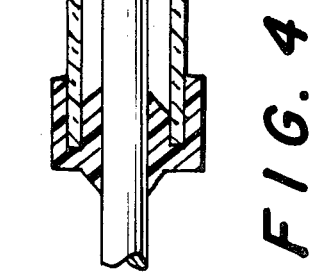

METHOD AND APPARATUS FOR COLLECTING AND/OR GROWING PROTECTED BIOLOGICAL SPECIMENS

This invention is generally directed to method and apparatus for collecting and/or growing protected biological specimens. It is particularly directed to a novel structure and method for obtaining, transporting and/or growing biological specimens which are completely protected from contamination at all times after initial capture.

The problem of protecting a biological specimen from contamination during and after its initial capture is an old one. That is, it is well known that unless special precautions are taken, a given biological specimen may inadvertantly become contaminated during the collection process and/or during transfer of the collected specimen to a growing medium or the like. Once thus contaminated, the worth of the specimen for diagnostic or research purposes may be greatly reduced or even eliminated.

Deep cavity cultures as well as shallow cavity cultures (e.g. abscesses, surgical incisions, etc.) are an everyday necessity in medicine, both human and veterinary. The results of these cultures must be accurate in order for a doctor to be certain of the condition and of the type of treatment necessary, if any. The uses vary from remedial to lifesaving, to status, as in the case of many veterinary uses. One such use would be in determining the bacterial count and type in the uterus of an equine mare prior to breeding.

Since the specimens are obtained in non-sterile environments, for the most part, it is imperative that the specimen be protected from contamination from the outer extremities of these cavities, as well as from air, which, for example, generally contains bacteria. Any contamination with bacteria from the air or outer extremities of the cavity would provide false or misleading diagnosis of the condition sought.

Certain prior attempts have been made to minimize contamination by inserting two tubes, one within the other, to the desired depth in the cavity. Upon insertion, the inner tube, or rod is extended past the end of the outer tube, and a cotton swab contained on the end of the inner tube is saturated with mucosa from the walls of the cavity at the desired point. Upon saturation, the inner tube is withdrawn into the outer tube and then both withdrawn as a unit to the outside air.

For the bacteria contained in the mucosa on the swab to survive and grow, they must be placed in a growth environment medium, most generally in the form of a sterile liquid or gel. This is generally in a test tube like container. The procedure is to remove the mucosa saturated swab from the outer tube and place it in the tube of growth medium, cutting or breaking off the tube and placing a stopper in the tube. It is then transported to the lab where the growing culture is identified by laboratory techniques.

Typical prior art approaches to this problem are illustrated in the following prior issued U.S. patents:

U.S. Pat. No. 3,513,830—Kalayjian (1970)
U.S. Pat. No. 4,136,680—Southworth (1979)
U.S. Pat. No. 4,235,244—Abele et al (1980)
U.S. Pat. No. 3,394,699—Koett (1968)
U.S. Pat. No. 3,674,007—Freis (1972)
U.S. Pat. No. 3,800,781—Zaluchi (1974)
U.S. Pat. No. 3,995,618—Kingsley et al (1976)
U.S. Pat. No. 4,023,559—Gaskell (1977)
U.S. Pat. No. 4,157,709—Schuster (1979)
U.S. Pat. No. 4,184,483—Greenspan (1980)
U.S. Pat. No. 4,223,093—Newman et al (1980)

Kalayjian and Abele et al are both typical of prior art approaches where a biological specimen collecting swab attached to the end of an elongated rod is protected within a outer hollow tube structure temporarily sealed with a cap-like seal at its distal end. In use, the sealed distal end of the rod and tube assembly is projected into an internal body organ or the like where the desired biological sample naturally resides. Thereafter, the rod is extended to displace the seal at the distal end of the tube and to expose the swab at the desired biological site. After the specimen has been collected on the swab, it is then withdrawn into the outer protective tube and the entire assembly is withdrawn from the body organ or the like. Later, the rod with the biological swab is transferred from the protective tube to a culture growth medium in a separate test tube or other structure. In this type of device, the protective seal on the distal end of the outer tube cannot be replaced to protect the collected sample as it is withdrawn from the body cavity and/or when it is later transported to the culture growth medium or the like in another structure. As will be appreciated, many types of bacteria can be seriously contaminated, and/or killed, by even brief exposure to oxygen in the air, or other gaseous, liquid or solid contaminants that may be encountered whenever the swab is not in a completely protected environment.

Southworth provides an apparatus which attempts to more completely protect the biological specimen. For example, the distal end of the outer hollow protective tube includes a hinged cap assembly that is designed to provide some protection both before and after the swab is used for collecting a biological specimen. Furthermore, provisions are made for withdrawing the collected specimen directly into an enlarged anterior chamber where a culture growth medium or the like is provided. However, the hinged protective cap structure in Southworth is not believed to provide true isolation or absolute protection from the ambient environment and, in any event, the overall multi-part apparatus appears to be relatively complex and expensive.

The remaining patents referenced above are typical of other types of instruments for obtaining biological specimen. However, none of them are believed to describe a structure which may be used for collecting the biological specimen and thereafter transporting it to a desired culture growth medium or the like in a completely protected environment, or in an anaerobic state.

Now, however, with this invention, a biological specimen may be collected at its natural biological site and thereafter maintained in a completely protected environment at all times while being transported away from the natural biological site and into the presence of desired biological growth materials, transport materials, release agents, etc.

My invention is new, unique and of great improvement over the prior art. While in some cases it is somewhat similar in outward appearance, the invention contains many new and novel features never before utilized in specimen capturing instruments.

I anticipate this invention to be used in several different areas of medicine, both human and veterinary. It will be used as a deep cavity instrument in many cases. It is however, useful for shallow cavities as well, such as abscesses, surgical incisions and etc. It will also be used for various types of cultures, and as a result, different forms of the invention will be utilized to accomplish them. They will all utilize the isolated and protective environment features of my invention, however.

A major area of medicine that my invention will now allow participation in, is the collecting of anaerobic specimens, as well as aerobic.

The exemplary embodiment of this invention utilizes an elongated hollow outer protective tube disposed about a longer inner rod member. In its initial state, prior to use, the forward ends of the rod and protective tube are substantially aligned while the rear end of the elongated inner rod extends beyond the rear end of the outer protective tube. A rear seal affixed to the rear end of the outer protective tube provides a slidable sealed support for the rod. The forward end of the rod includes a cap-like seal which normally sealingly engages the forward end of the tube so as to define a coaxial sealed cavity between the rear and front seals, the inside wall of the outer protective tube and the outside surface of the inner rod.

This sealed cavity is divided into two separate chambers by a disk-like seal attached to the rod at a location intermediate the rear and front seals. This disk-like seal normally provides a slidable sealing engagement with the inside wall of the outer protective tube. However, the periphery of the disk-like seal may be deformed whenever a pressure differential of sufficient magnitude exists thereacross so as to permit passage of material from one chamber to the other as the relative volumes of these two chambers are altered by sliding motion of the inner rod.

In the exemplary embodiment, absorbent material or other specimen collecting structure is affixed to the forward end of the rod just behind the forward seal so as to collect a desired specimen whenever the rod is moved forwardly of the outer tube. Thereafter, the rod is moved rearwardly of the outer tube so as to invert the cap-like forward seal so that it provides a sliding seal with the inside wall of the outer tube as it is withdrawn into the tube. At the same time, a culture growth medium or the like may be provided in the rear chamber behind the disk-like seal. If so, upon retraction of the rod, the volume of the rear chamber is reduced so as to increase the material pressure in that chamber and to cause the culture growth medium to pass by the disk-like seal into the forward chamber so as to support life of the biological sample. Preferably, the inverted cap-like forward seal is also capable of further deflection so as to permit outwardly directed passage of excess material as the combined volume of the forward and rear chambers is collectively reduced by further retraction of the rod.

The invention permits effective isolation of any desired substance in the tube, either gas, liquid or solids, from the outer environment. These include, but are not limited to, various transport materials, growth materials, selective growth materials or a combination of desired materials. The solid materials would most likely be on the walls. In other cases, the various desired material would be affixed to the inner core rod or tube, at some point aft of the absorbent material, but forward of the intermediate disk-like seal.

The purpose of this arrangement would be to allow the specimen to be obtained on the swab, retracted into the protective outer tube, and then retracted further into the desired, selected material, which in this case could be a combination growth and release agent that would soften the selected medium and allow it to saturate and mix with the specimen, thereby enabling immediate growth of the culture. Since the specimen was obtained in an absolute anerobic state, and the invention maintains this absolute isolation, very accurate cultures can be obtained.

It must be understood that my invention will obtain, and maintain, a specimen in an absolute "as obtained" state, either aerobic or anaerobic.

Stated somewhat differently, the present exemplary embodiment includes two concentric cylindrical structures, the inner one of which may be solid. Such cylindrical structures may be formed, for example, of glass or the like and are relatively slidable along their substantially coincident axes. A disk-like flexible seal retains a culture growth medium or the like between it and a rear seal in the coaxial space between the two cylindrical members. At the forward end of the inner cylinder, absorbent material is mechanically affixed for gathering the sample specimen and a special cap-like seal is affixed to the front end of the inner cylinder. Before use, the coaxial space between the disk-like seal and the forward end of the inner cylinder may be filled with a non-contaminated, non-reactive gas.

Thus, before use, the absorbent material and the culture growing medium or the like are all protected from the outside environment by the outer cylindrical structure which has a permanent rear seal and a cap-like seal at its forward end attached to the inner cylinder. After insertion into an internal organ or the like, the inner tube is projected forwardly so as to expose the absorbent material and gather a specimen. Thereafter, while the outer cylinder is still in place internally of the organ, the inner cylinder is withdrawn rearwardly. As the disk-like seal comes into contact with the liquid, gaseous, gelatinous or particularized culture growth medium or the like, it is deflected so as to allow this material to flow into contact with the specimen on the absorbent material. At the same time, the cap-like seal inverts and continues to provide sliding sealable protection against the ambient environment for the specimen and for the growth medium or the like. On the other hand, any excess material is permitted to pass outwardly past the inverted cap-like seal as the inner cylinder is withdrawn rearwardly.

After the inner cylinder has been withdrawn from the internal organ and also completely withdrawn rearwardly to the maximum desired extent in the outer protective tube, any excess rearward length of the inner cylinder and/or excess forward length of the outer cylinder can be mechanically detached (e.g. by breaking along preformed break lines or the like) and the culture left to grow in a growth medium or the like. In this fashion, a specimen may be collected and placed within a growth medium (or any other desired medium) without any substantial opportunity for contamination.

The unique arrangement of rear, middle and forward seals just described actually may be used to realize several important functions. First of all, it may be used to isolate the culture growth medium or the like from the swab used to capture the specimen until such contact is desired (e.g., after the biological specimen has actually been captured). As already explained, at that time, as the inner rod and seal is drawn rearwardly, the middle seal is designed so as to permit material (gas, liquid, gelatinous, etc.) to pass by the seal into the forward chamber where it is permitted to saturate the biological specimen on the swab which is, after all, still isolated from the outside environment by the forward seal.

In addition, this unique arrangement of seals including the middle disk-like seal can be useful in obtaining increased volumes of specimen material than is possible with just a swab device. For example, in the case of surgical incisions, urine, abscesses, blood, etc., a doctor or veterinarian would often like to obtain a greater volume of specimen material than can be obtained with a simple prior art swab device. By making the disk-like middle seal somewhat stiffer, it can be caused to create a negative or suction pressure within the forward chamber as the rod is being retracted rearwardly at the natural biological site such that available biological specimen material may be effectively aspirated into the forward chamber before it is again sealed.

The rear seal on the outer protective tube discussed previously may be a single flange chevron or a plural flange bi-directional chevron-type seal. In any event, unless some further precaution is taken, it is conceivable that the normally extended area of the inner rod may become contaminated and that some of this contamination may pass the rear seal into the rearward compartment defined by the rear, middle and forward seals. To ensure against such possible contamination materials passing the rear seal, an extra outer protective seal may be provided about this area of the inner rod. For example, a thin dip-coating layer of a silicone elastomer may be provided to encompass the entirety of the normally rearwardly extended portion of the inner rod as well as the rear end of the outer protective tube. In use, as the inner rod is moved forwardly, the thin flexible silicone coating is simply stripped from the rod at the rear seal area (the thin material might actually "pile up" against the rear seal). In this manner, any possible contamination via the normally extended surface of the inner rod is completely eliminated.

These as well as other objects and advantages of this invention will be more completely understood by study of the following detailed description of the presently preferred exemplary embodiment of the invention taken in conjunction with the accompanying drawings, of which:

FIG. 1 is a cross-sectional view of an exemplary embodiment of this invention in its initial condition prior to actual use;

FIG. 2 is a cross-sectional diagram like that of FIG. 1 but showing the inner rod in a forwardly extended position as it would be during capture of a biological specimen;

FIG. 3 is a cross-sectional depiction similar to FIG. 1 but showing the inner rod in a rearwardly protracted position; and FIG. 4 is a cut-away cross-sectional view of an alternate rear seal employing plural bi-directional chevron-type seal flanges.

The exemplary embodiment shown in FIG. 1 includes an elongated outer protective glass cylinder 10 and an inner glass rod 12 having an even greater length. For purposes of description, the left end of the cylinder and rod (which might also be thought of as a piston 12 and cylinder 10 assembly) will be referred to as the "rear" end while the right end will be referred to as the "forward" end.

As may be observed in FIG. 1, the outside diameter of the rod is materially less than the diameter of the inside wall of the tube or cylinder 10. As should be appreciated, this then creates a coaxial space in which various materials may be contained. This coaxial space is divided by a disk-like seal 14 affixed to the rod 12 into a first or front chamber 16 and a second or rear chamber 18. The first chamber 16 is normally sealed at the forward end by a cap-like seal 20 attached to the distal end of the rod 12 and sealingly engaging the distal end of the cylinder 10. The rear end of chamber 18 is sealed by a chevron-type rear seal structure 22. Absorbent material 24 (or other specimen capturing structure) is also affixed near the distal end of rod 12 but behind the front seal 20. The second or rear chamber 18 may be initially filled with a culture growth medium, a culture transport medium, a biological release agent, etc. As shown in FIG. 1 by stipling, this filling may, for example, normally fill substantially all of the rear chamber 18. The remainder of chamber 18 and chamber 16 are normally filled with a non-contaminated, non-reactive gas or liquid.

In this initial condition, just prior to use, the rear seal 22 and the disk-like middle seal 14 provide slidable sealing contact between the rod 12 and cylinder 10.

After the distal end of the structure shown in FIG. 1 is inserted to the desired site of a biological specimen (e.g., deep within an internal organ 21 of a human or animal), the rod 12 is moved forwardly to a position like that shown in FIG. 2 so as to expose the absorbent material 24 and to unseal the distal end of cylinder 10 and cavity 16. It will be seen that by moving the rod 12 forwardly, the volume of cavity 18 has been increased while the volume of cavity 16 has been decreased (and the latter has been unsealed as well so as to permit capture of a biological specimen). The disk-like middle seal 14 has a flexible periphery that may be chosen to have a desired degree of stiffness by choosing its thickness, material, etc. as will be appreciated. In some embodiments, it may be desirable to make the periphery of the disk-like seal 14 quite flexible such that part of the inert filling from chamber 16 will actually flex the periphery of the middle seal 14 and pass into the chamber 18 when rod 12 is moved forwardly thus relieving a relatively lower pressure in chamber 18 caused by this movement of the rod 12. On the other hand, in the other embodiments, it may be desired to make the disk-like seal somewhat stiffer in its periphery so as to leave a relatively lower pressure in chamber 18 as the rod 12 is extended forwardly. In this latter instance, when the rod 12 is then again moved rearwardly to again compress the contents of chamber 18, a relatively lower pressure area may be created in chamber 16 so as to draw additional volumes of biological specimen into that chamber.

Typically, when the instrument is in the extended condition shown at FIG. 2, the operator will be holding the rear end of the assembly and thereby move the distal end of the extended and opened assembly within the internal organ so as to ensure absorption of the desired biological specimen within the absorption material 24, for example. Thereafter, the rod 12 is moved rearwardly to a position such as that shown in FIG. 3. As such rearward motion occurs, the cap-like seal 20 inverts to the shape shown in FIG. 3 so as to provide sliding sealing contact with the inside walls of the outer cylinder 10. At the same time, reduction in volume of chamber 18 caused by rearward movement of the rod 12 produces a pressure buildup until the periphery of the disk-like middle seal 14 is flexed so as to permit the pre-filled material in chamber 18 to pass into chamber 16 and into direct contact with the biological specimen. Any excess material in the now shrinking combined volume of chambers 18 and 16 is also permitted to pass outwardly past the inverted cap-like seal 20 as also shown FIG. 3.

In this manner, the biological specimen has been captured at its natural site and transferred to a desired growth medium or the like wholly within the protected coaxial sealed chambers 18 and 16. The only conceivable source of contamination might be via the left-most normally extended surface of the rod 12. If this surface becomes contaminated, it is conceivable that some of the contamination might pass by the rear chevron-type seal 22 and into chamber 18 as the rod is moved forwardly to the position shown in FIG. 3. However, to prevent any such possible contamination, a thin protective outer seal 26 is preferably provided. For example, this thin outer seal 26 may be provided in the form a dip coating to a point past the forward end of the rear chevron seal 22. Such a thin layer (e.g., of silicone elastomer or similar material) is then simply stripped from the rod at a point adjacent the chevron seal as the rod moves forwardly into the outer tube. This thin material may "pile up" against the rear chevron seal as shown in FIG. 2 during the extension process depicted in FIG. 2.

During withdrawal to the rearward position shown in FIG. 3, the thin flexible seal 26 may break or otherwise loose its sealing properties. However, such would be of no consequence since the inside pressure of the assembly is then above the ambient (thus preventing inward passage of material past seals, and the like). Furthermore, when in the preliminary ready-to-be-used state shown in FIG. 1, any lower pressure within the assembly would be prevented from equilization with the ambient by the dip-coat seal 26 and the cap-like seal 20. That is, any lowered internal pressure (from whatever cause) would actually enhance the sealing at both ends of the outer protective tube 10. In this manner, the thin protective seal 26 not only prevents any possible contamination of chamber 18 via the rear surface of rod 12, it also actively ehances the sealing of the instrument against ambient conditions while stored in a ready-to-use condition.

The rear, middle and cap-like forward seal are preferably made of medical grade silicone elastomer of similar suitable material. The rear seal may be of a single flange chevron-type as shown in FIGS. 1-3 or a plural flange, bi-directional chevron-type of seal as shown in FIG. 4. Such a bi-directional seal may provide better sealing action both from within and without and may be especially useful, for example, if the thin protective outer shield 26 is not used.

As should now be appreciated, the trailing end of the outer tube contains a seal of suitable material to isolate the outer environment, and designed to contain internal pressure in the outer tube, sealing the inner tube with the outer tube. The forward end of the inner tube contains a cap-like seal of suitable material that is attached to the forward end of the inner tube. When positioned for initial insertion into a deep cavity, for example, the forward cap-like seal is positioned at the leading edge of the outer tube, thereby sealing the inner tube from any outside environment, either air or liquid.

Directly behind the cap-like seal on the forward end of the inner tube is an area containing an absorbent material to collect mucosa. Rearward from the absorbent material a suitable distance is a seal of suitable material much like a flexible disk that is fastened to the inner tube, that seals the area between the inner tube and the inner surface of the outer tube. This seal is designed in a manner that creates separate chambers within the outer tube as to air or liquid movement under normal atmospheric pressure. However, when the inner tube is drawn rearward in the outer tube, the above atmospheric pressure created in the rear of the outer tube between the rear seal and the disk-like seal will cause the disk-like seal to deflect forward and pass any buildup of pressure or liquid past the seal into the forward compartment, the point of said passing being determined by seal design.

The area behind the disk-like seal contains a certain quantity of growth medium or other suitable material, separated from the forward absorbent material by the disk-like seal. Moving the inner tube fully rearward, relative to the outer tube causes the growth medium to move past the disk-like seal and surround and saturate the mucosa saturated absorbent material. The forward cap-like seal is designed in such a manner that it deflects forward when contacting the outer tube due to the relative rearward movement of the inner tube. This forward cap-like seal is designed to pass pressure buildup past its sealing surface to eliminate a buildup of pressure between the disk-like seal and the cap-like seal as they move rearward, relative to the outer tube.

The overall length of the culture device will vary with use. In the case of a equine uterine culture, the instrument will be 20 to 24 inches long overall, with the outer tube diameter 5/16 inch. The length and diameter will vary with various models. Human instruments will be designed with finger loops for one handed use, in some cases.

Many times the doctor would like to be able to obtain more specimen material than is possible with just a small swab device, as in the case of surgical incisions, urine, abscesses, blood, to name a few. With my invention the unique middle disk-like seal can be varied by design to allow specific amounts of pressure, either plus or minus, to be created by movement relative to the outer tube, and with varying volume of the rearward sealed compartment relative to the amount of liquid material it contains. This allows the instrument to be used as a suction device, to permit larger amounts of specimen material to be obtained upon withdrawal of the inner rod containing the swab and the disk-like seal. After the forward end is immersed in the specimen liquid, the swab becomes saturated, and in addition, upon withdrawal, a low pressure area is created in the outer tube, thereby drawing in additional specimen material.

If it is desired to obtain additional fluid, further rearward movement of the rod will cause aspiration of additional fluids into the tube forward of the forward seal, the volumetric amount being determined by the stiffness and design of the forward and middle seals. Forward movement of the rod will expell the fluid. Stopping forward movement of the rod prior to the forward seal emerging from the outer tube would still maintain the sealed specimen in the isolated, as taken, state.

To explain one possible use, it will be assumed that a veterinary doctor desires a culture of the uterine mucosa of a mare. Standard procedure is to dilate the vaginal cavity with the usual instruments, exposing the cervix. My invention is then removed from a protective sterilized container in sterile condition. The inner and outer tubes are in position at front so the forward cap-like seal seals the inner and outer tube. The cap-like seal may also be shaped for easy insertion. The inner tube, being several inches longer than the outer tube, protrudes from the rear of the outer tube. The rearward compartment of the outer tube between the rear seal and the disk-like seal contains growth medium material.

The doctor inserts the instrument into the cervix as a unit to the desired depth. The outer tube is then held and the inner tube is extended forward, relative to the outer tube, the distance desired. It is normal to swab back and forth several times to assure complete saturation of the absorbent material with the mucosa from the uterus wall. The inner tube is then withdrawn rearwardly into the outer tube, thereby deflecting the forward cap-like seal forward and reversing its surface. This assures that any possible contamination on the outside of the seal remains on the outside, away from the specimen. The inner tube is withdrawn into the outer tube several inches past the original position before withdrawal of the complete instrument. Upon withdrawal, the specimen is completely protected from any contamination by any means.

The inner tube is then completely withdrawn to the rear of the outer tube, displacing the growth medium material past the disk-like seal into the mucosa saturated absorbent area, thereby surrounding the mucosa and starting growth of the culture in the original isolated environment, completely free from any outside contamination.

The rear inner tube can be cut or broken off an inch or two from the back end of the outer tube, if desired (as indicated in FIG. 3). The outer tube can likewise be shortened as desired at any point forward of the deflected cap-like seal. Placement in a suitable container, such as a zip-lock plastic bag, with the labeling area necessary for identifying data filled in, readies the culture for transport to the laboratory for analysis.

If desired, removal at the lab may be simply accomplished by rolling the rear seal rearward and pulling the inner tube rearward relative to the outer tube, and the outer tube discarded.

While only one exemplary embodiment of this invention has been described in detail, those in the art should appreciate that there are many possible variations and modifications of this exemplary embodiment which may be made without departing from the novel and unique features of this invention. Accordingly, all such modifications and variations are intended to be included within the scope of the following appended claims.

What is claimed is:

1. An instrument for obtaining a biological specimen, said instrument comprising:
    an elongated hollow outer protective member having a rear end and a front end;
    an elongated inner member also having rear and front ends with a portion of said inner member being slidably disposed within said outer member for relative motion in either of two opposed directions;
    a rear seal affixed to said outer member at its rear end and slidably sealed thereat to said inner member;
    a flexible front seal means disposed at the front of said inner member and providing a sealed connection between said outer and said inner members when their front ends are juxtaposed and also providing a slidable sealed connection between said outer and said inner members when said inner member is relatively moved toward the rear of said outer member while also flexing to provide a passageway therepast towards said front end in response to a pressure differential thereacross;
    said rear and front seals defining a sealed cavity between said inner and outer members which can be controllably opened at the front ends of the members by relatively moving the inner member toward the front end of the outer member, the volume of said sealed cavity being controllably reduced by relatively moving the inner member toward the rear end of the outer member to thereby cause a pressure differential across said front seal; and
    a specimen capturing structure disposed on said inner member between said front and rear seals.

2. An instrument as in claim 1 further comprising:
    a flexible middle seal disposed on said inner member between said rear and front seals,
    said flexible middle seal providing a slidable sealed connection between said outer and inner members thus separating and defining front and rear chambers within said sealed cavity having relative dimensions corresponding to the relative positions of said inner and outer members;
    a pre-filled flowable material disposed in at least said rear chamber;
    said flexible middle seal being constructed to permit passage of said material between said chambers when the pressure of material in one chamber exceeds by a predetermined amount the pressure of material in the other chamber due to relative movement of said inner and outer members.

3. An instrument as in claim 2 wherein said rear chamber contains a culture growth medium.

4. An instrument as in claim 2 or 3 wherein said front seal includes a flexible periphery to permit passage of material out of said sealed cavity as the pressure of material therein is increased by relative movement of said inner and outer members.

5. An instrument as in claim 4 wherein said inner and outer members comprise concentric cylinders and wherein said rear seal comprises at least one seal fixedly attached to the rear end of said outer member and having a sloping circumferential flange surface terminating in sealing engagement with said inner member.

6. An instrument as in claim 5 wherein said rear seal comprises a seal having at least two spaced apart and sloping circumferential flange surfaces terminating in sealing engagement with said inner member.

7. An instrument as in claim 5 wherein said front seal comprises a seal fixedly attached to the front end of said inner member and having an outer flange for sealingly engaging the front end of said outer member but capable of being inverted to sealingly engage the inside wall of said outer member when drawn therein by relative movement of said inner member.

8. An instrument as in claim 7 wherein said middle seal comprises a disk-like seal fixedly attached to said inner member and having a flexible outer periphery in bi-directional sliding engagement with the inside wall of said outer member and also capable of being flexed out of sealing engagement with the inside wall by a predetermined pressure differential on opposite sides of the disk-like seal.

9. An instrument as in claim 8 wherein said front, middle and rear seals are formed of a medical grade silicone elastomer.

10. An instrument as in claim 8 further comprising:
    a protective elastic casing formed about the rear ends of said inner and outer members which is capable of being deformed and stripped from said inner member as it is moved into said outer member.

11. An instrument as in claim 1, 2 or 3 further comprising:
a protective elastic casing formed about the rear ends of said inner and outer members which is capable of being deformed and stripped from said inner member as it is moved into said outer member.

12. Apparatus for collecting a biological specimen, said apparatus comprising:
first and second elongated members slidably movable with respect to one another in each of two opposing directions, said second member surrounding at least a portion of said first member and having a rear seal fixed to said second member and slidably disposed with respect to said first member;
a flexible middle seal means fixedly secured to said first member and slidably disposed with respect to the second member; and
a flexible front seal means also fixedly secured to said first member but at a location spaced from said middle seal whereby first and second chambers are defined by the spaces between said first and second members and the seals, said first and second chambers having controllably variable relative volumes such that relative sliding motion of the members in one direction increases the volume of said first chamber and relative sliding motion in the opposite direction decreases the volume of said first chamber, said middle seal being capable of separating said first and second chambers except when flexed to provide a passageway therebetween in response to a predetermined pressure differential thereacross caused by a decrease in volume of said first chamber, said front seal sealing said second chamber except when controllably unsealed by said sliding motion in one direction of the members to permit capture therein of a desired biological specimen and said front seal thereafter capable of being flexibly deformed to enter and reseal said second chamber while being sealingly disposed with respect to said second member during said sliding motion in the opposite direction of the members.

13. Apparatus as in claim 12 further comprising a biological growth material disposed within said first chamber.

14. Apparatus as in claim 12 or 13 wherein said first and second members comprise a rod and cylinder respectively and wherein said first and second chambers comprise sections of a coaxial space defined between said cylinder and said rod, said rod being longer than said cylinder which cylinder is disposed around said rod.

15. Apparatus as in claim 14 wherein said rod includes a distal end and said front seal is affixed to said distal end of said rod.

16. Apparatus as in claim 15 wherein said cylinder has a rear end at which said rear seal is affixed and further comprising an outer protective shield layer disposed about the rod and said rear end of the cylinder.

17. Apparatus as in claim 16 further comprising an absorbent specimen collecting structure affixed to said rod near said front seal.

18. Apparatus as in claim 15 further comprising an outer protective shield layer disposed about the end of the cylinder and rod opposite said front seal.

19. An instrument for obtaining a biological specimen, said instrument comprising:
a coaxial piston and surrounding cylinder assembly defining a coaxial cavity therebetween, said piston being longer than said surrounding cylinder and having an outer diameter smaller than the inside diameter of said cylinder;
first, second and third seals, each seal being fixedly attached to one of said piston and said cylinder and being slidingly engaged with the other of said piston and said cylinder, said seals being spaced apart from one another along said coaxial cavity to define first and second sealed chambers therewithin, said third seal being affixed to said piston whereby said second chamber is selectively unsealed and opened by moving said piston within said cylinder;
specimen capturing structure normally disposed within said second chamber so as to be selectively exposed when that chamber is selectively unsealed and opened;
at least one of said seals being relatively moveable with respect to at least one other of the seals when said piston is moved so as to change the relative volumes of said chambers; and
said second seal being flexible to define a passageway between said chambers in response to a predetermined pressure differential developed thereacross due to piston movements which cause a change in the relative volumes of said chambers.

20. An instrument as in claim 19 wherein said first chamber contains a culture growth medium.

21. An instrument as in claim 19 wherein said third seal is also flexible to define a passageway out of said second chamber as the pressure therein is increased by movement of said piston.

22. An instrument as in claim 19, 20 or 21 further comprising:
a protective elastic casing formed about a predetermined portion of the piston and cylinder assembly which is deformable and strippable from said piston as the piston is moved into said cylinder.

23. An instrument for obtaining a biological specimen, said instrument comprising:
an outer hollow tube having first and second ends;
an inner rod having first and second ends and disposed within said outer tube;
said inner rod having a greater length than said outer tube;
a specimen capturing structure affixed to said inner rod;
a rear seal affixed to the first end of said outer tube and in slidably sealed engagement with said inner rod;
a front seal affixed to the second end of said inner rod and defining a sealed connection with the second end of said outer tube which may be controllably opened by sliding movement of said inner rod; and
a middle seal affixed to the inner rod at a point between said rear seal and specimen capturing structures, said middle seal defining a slidable sealed connection with the inside wall of said outer tube.

24. An instrument as in claim 23 wherein said front seal is deformable to define a slidable sealed connection with the inside wall of said outer tube upon being drawn thereinto by movement of said inner rod.

25. An instrument as in claim 24 wherein said outer hollow tube is at least partially filled with flowable material and wherein said front seal is also deformable to permit passage of excess said material therepast if directed toward said second end of the outer tube with sufficient pressure.

26. An instrument as in claim 24 or 25 wherein said front seal has an outer end for sealing contact with the second end of the outer tube until deformed by being moved into said outer tube.

27. An instrument as in claim 23 wherein said outer hollow tube is at least partially filled with flowable material and wherein said middle seal is disk-like in shape with a flexible periphery that is deformable to permit material passage therepast in response to a predetermined pressure differential developed thereacross by movement of said inner rod.

28. An instrument as in claim 23 wherein said specimen capturing structure is affixed near the second end of said inner rod.

29. An instrument as in claim 23, 24, 25, 27 or 28 wherein a space between said rear seal and said middle seal contains at least one material chosen from the following list of materials:

a. a biological culture growth medium, b. a biological culture transport material, c. a biological release agent.

30. An instrument as in claim 23, 24, 25, 27 or 28 wherein at least one of the two chambers formed between said back, middle and front seals contains at least one material chosen from the following list of materials:

a. a biological culture growth medium, b. a biological culture transport material, c. a biological release agent.

31. An instrument as in claim 23, 24, 25, 27 or 28 further including an outer protective seal over an extended portion of the first end of said inner rod, said outer protective seal comprising a layer of material disposed over at least said extended portion of the inner rod and strippable therefrom as the first end of the inner rod is moved towards said outer tube.

32. An instrument as in claim 31 wherein said outer protective seal comprises an elastomer coating encapsulating said extended portion of the inner rod and the first end of the outer tube.

33. A method for collecting a biological specimen using a collection device having first and second members relatively movable in opposing first and second directions and defining first and second chambers having controllably variable relative volumes separated by a flexible middle seal fixedly secured to said first member and slidably received by the second member, said first chamber being increased in volume by movement of said first member in said first direction and being decreased in volume by movement of the first member in the second direction, said second chamber being bounded by a front seal fixedly secured to said first member and sealingly engagable with said second member which front seal can be selectively unsealed by relative movement of said first member in said first direction and having a pre-filled material in at least said first chamber, said method comprising the steps of:

placing said front seal of said second chamber at the natural site of a desired biological specimen;

unsealing said front seal at said site to permit entry of said biological specimen into said second chamber by relative movement of said first member in said first direction;

resealing said front seal at said site to protect the biological specimen collected into said second chamber by relative movement of said first member in said second direction; and reducing the volume of said first chamber by further relative movement of said first member in said second direction so as to force said pre-filled material therein past said middle seal into said second chamber and into contact with said biological specimen.

34. A method as in claim 33 wherein said resealing step includes the step of initially sliding said middle seal within said second member sufficiently quickly to create a lowered pressure in said second chamber that acts to aspirate additional biological culture material into said second chamber prior to actual resealing of the second chamber.

35. A method as in claim 33 wherein said first and second members respectively comprise a rod disposed within a cylinder and wherein said chambers are formed within said cylinder and outside said rod which is disposed within that cylinder and wherein said unsealing step includes the step of sliding said rod into said cylinder and the step of stripping said protective outer layer from said rod as the rod enters the cylinder.

* * * * *